(12) United States Patent
Grootaert et al.

(10) Patent No.: US 8,906,821 B2
(45) Date of Patent: *Dec. 9, 2014

(54) CURING COMPOSITIONS FOR FLUOROPOLYMERS

(75) Inventors: Werner M. A. Grootaert, Oakdale, MN (US); Kim M. Vogel, Lake Elmo, MN (US); Dennis E. Vogel, Lake Elmo, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 167 days.

This patent is subject to a terminal disclaimer.

(21) Appl. No.: 13/322,001

(22) PCT Filed: Jun. 24, 2010

(86) PCT No.: PCT/US2010/039730
§ 371 (c)(1),
(2), (4) Date: Nov. 22, 2011

(87) PCT Pub. No.: WO2010/151610
PCT Pub. Date: Dec. 29, 2010

(65) Prior Publication Data
US 2012/0065321 A1    Mar. 15, 2012

Related U.S. Application Data

(60) Provisional application No. 61/220,441, filed on Jun. 25, 2009.

(51) Int. Cl.
| | | |
|---|---|---|
| *C08F 14/18* | (2006.01) | |
| *C08F 214/18* | (2006.01) | |
| *B01J 27/14* | (2006.01) | |
| *B01J 31/02* | (2006.01) | |
| *C07C 259/06* | (2006.01) | |
| *C08F 4/00* | (2006.01) | |
| *C08K 5/05* | (2006.01) | |
| *C08K 5/19* | (2006.01) | |
| *C08K 5/29* | (2006.01) | |
| *C08K 5/315* | (2006.01) | |
| *C08K 5/50* | (2006.01) | |
| *C08L 27/12* | (2006.01) | |
| *C08K 5/00* | (2006.01) | |
| *C08L 27/18* | (2006.01) | |

(52) U.S. Cl.
CPC .............. *C08F 214/18* (2013.01); *B01J 27/14* (2013.01); *B01J 31/0205* (2013.01); *B01J 31/0234* (2013.01); *C07C 259/06* (2013.01); *C08F 4/00* (2013.01); *C08F 214/184* (2013.01); *C08K 5/0025* (2013.01); *C08K 5/05* (2013.01); *C08K 5/19* (2013.01); *C08K 5/29* (2013.01); *C08K 5/315* (2013.01); *C08K 5/50* (2013.01); *C08L 27/12* (2013.01); *C08L 27/18* (2013.01); *C08L 2205/02* (2013.01)
USPC ........ 502/167; 252/326.3; 252/340; 252/341; 252/343; 252/379; 526/247; 526/253; 526/255; 524/380; 524/433; 524/346; 528/275; 528/282; 528/308.6; 502/150

(58) Field of Classification Search
USPC ...................... 525/326.3, 340, 341, 343, 379; 526/247, 253, 255; 524/380, 433, 436; 528/275, 282, 308.6; 502/150, 167
See application file for complete search history.

(56) References Cited

U.S. PATENT DOCUMENTS

| | | |
|---|---|---|
| 3,117,996 A | 1/1964 | Chambers |
| 3,523,132 A | 8/1970 | Dorfman et al. |
| 3,546,186 A | 12/1970 | Gladding et al. |
| 3,686,143 A | 8/1972 | Bowman |
| 3,740,369 A | 6/1973 | Proskow |

(Continued)

FOREIGN PATENT DOCUMENTS

| | | |
|---|---|---|
| EP | 0 140 207 A2 | 5/1985 |
| EP | 0 429 250 A2 | 5/1989 |

(Continued)

OTHER PUBLICATIONS

Definition of "Dry" from Merriam Webster Online Dictionary. Retrieved from the internet Feb. 2014.*

(Continued)

*Primary Examiner* — Robert C Boyle
(74) *Attorney, Agent, or Firm* — C. Michael Geise

(57) ABSTRACT

A catalyst composition comprising a cation and an anion of the formula $A_n{}^{q-}Q_p{}^{m+}$, wherein m, n, p, and q are positive integers, wherein m*p=n*q, wherein $Q^{m+}$ is an organo onium, and $A^{q-}$ is an anion, provided that at least one $A^{q-}$ is selected from the formula (I) wherein each R independently is H, halo, alkyl, aryl, aralkyl, or cycloalkyl, and which also may be halogenated, fluorinated, or perfluorinated, wherein two or more of R and R' groups may together form a ring, wherein each R group independently may contain one or more heteroatom(s), wherein R' can be the same as R, with the proviso that R' cannot be halo, and wherein the catalyst composition is essentially free of hydrocarbon containing alcohol. Also provided are a fluoropolymer composition including this curative, a method of making a fluoropolymer, and fluoropolymer articles containing curable or cured fluoropolymer compositions.

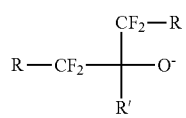

(I)

23 Claims, No Drawings

(56) References Cited

U.S. PATENT DOCUMENTS

| | | |
|---|---|---|
| 3,752,787 A | 8/1973 | Brunner |
| 4,035,565 A | 7/1977 | Apotheker et al. |
| 4,259,463 A | 3/1981 | Moggi et al. |
| 4,281,092 A | 7/1981 | Breazeale |
| 4,287,320 A | 9/1981 | Kolb |
| 4,335,238 A | 6/1982 | Moore et al. |
| 4,358,559 A | 11/1982 | Holcomb et al. |
| 4,446,270 A | 5/1984 | Guenthner et al. |
| 4,487,903 A | 12/1984 | Tatemoto et al. |
| 4,550,132 A | 10/1985 | Capriotti |
| 4,564,662 A | 1/1986 | Albin |
| 4,645,799 A | 2/1987 | Wachi et al. |
| 4,649,045 A | 3/1987 | Gaske et al. |
| 4,677,137 A | 6/1987 | Bany et al. |
| 4,734,465 A | 3/1988 | Moggi et al. |
| 4,758,618 A | 7/1988 | Ito et al. |
| 4,762,891 A | 8/1988 | Albin et al. |
| 4,833,212 A | 5/1989 | Yamada et al. |
| 4,882,390 A | 11/1989 | Kolb |
| 4,886,862 A | 12/1989 | Kuwamura et al. |
| 4,912,171 A | 3/1990 | Grootaert et al. |
| 4,948,853 A | 8/1990 | Logothetis |
| 4,972,038 A | 11/1990 | Logothetis |
| 4,983,680 A | 1/1991 | Ojakaar |
| 5,032,655 A | 7/1991 | Moore |
| 5,077,178 A | 12/1991 | Herbert et al. |
| 5,110,983 A | 5/1992 | Lau et al. |
| 5,262,490 A | 11/1993 | Kolb et al. |
| 5,266,650 A | 11/1993 | Guerra et al. |
| 5,268,405 A | 12/1993 | Ojakaar et al. |
| 5,284,611 A | 2/1994 | Grootaert et al. |
| 5,285,002 A | 2/1994 | Grootaert |
| 5,319,025 A | 6/1994 | Weigelt |
| 5,349,093 A | 9/1994 | Oka et al. |
| 5,371,143 A | 12/1994 | Novak et al. |
| 5,378,782 A | 1/1995 | Grootaert |
| 5,384,374 A | 1/1995 | Guerra et al. |
| 5,409,998 A | 4/1995 | Chiodini et al. |
| 5,451,625 A | 9/1995 | Fukushi |
| 5,527,861 A | 6/1996 | Logothetis |
| 5,545,693 A | 8/1996 | Hung et al. |
| 5,554,680 A | 9/1996 | Ojakaar |
| 5,565,512 A | 10/1996 | Saito |
| 5,585,449 A | 12/1996 | Arcella et al. |
| 5,591,804 A | 1/1997 | Coggio et al. |
| 5,621,145 A | 4/1997 | Saito et al. |
| 5,637,648 A | 6/1997 | Saito et al. |
| 5,639,837 A | 6/1997 | Farnham et al. |
| 5,654,375 A | 8/1997 | Jing et al. |
| 5,668,221 A | 9/1997 | Saito et al. |
| 5,677,639 A | 10/1997 | Masiewicz |
| 5,681,881 A | 10/1997 | Jing et al. |
| 5,700,879 A | 12/1997 | Yamamoto |
| 5,728,773 A | 3/1998 | Jing et al. |
| 5,756,588 A | 5/1998 | Kolb et al. |
| 5,767,204 A | 6/1998 | Iwa |
| 5,789,489 A | 8/1998 | Coughlin et al. |
| 5,789,509 A | 8/1998 | Schmiegel |
| 5,824,749 A | 10/1998 | Sonoi et al. |
| 5,877,264 A | 3/1999 | Logothetis et al. |
| 5,891,965 A | 4/1999 | Worm |
| 5,910,552 A | 6/1999 | Saito et al. |
| 5,945,477 A | 8/1999 | DeSimone et al. |
| 6,077,609 A | 6/2000 | Blong et al. |
| 6,114,452 A | 9/2000 | Schmiegel |
| 6,211,319 B1 | 4/2001 | Schmiegel |
| 6,245,879 B1 | 6/2001 | Kelsey et al. |
| 6,255,535 B1 | 7/2001 | Schulz |
| 6,255,536 B1 | 7/2001 | Worm |
| 6,270,901 B1 | 8/2001 | Parsonage et al. |
| 6,281,296 B1 | 8/2001 | McLachlan et al. |
| 6,294,627 B1 | 9/2001 | Worm |
| 6,465,576 B1 | 10/2002 | Grootaert et al. |
| 6,482,522 B1 | 11/2002 | Parsonage et al. |
| 6,482,979 B1 | 11/2002 | Hintzer et al. |
| 6,593,416 B2 | 7/2003 | Grootaert et al. |
| 6,638,999 B2 | 10/2003 | Bish et al. |
| 6,657,012 B2 | 12/2003 | Grootaert et al. |
| 6,657,013 B2 | 12/2003 | Grootaert et al. |
| 6,706,193 B1 | 3/2004 | Burkard et al. |
| 6,720,360 B1 | 4/2004 | Grootaert et al. |
| 6,794,457 B2 | 9/2004 | Grootaert et al. |
| 6,803,425 B2 | 10/2004 | Hintzer et al. |
| 6,844,388 B2 | 1/2005 | Grootaert et al. |
| 6,846,880 B2 | 1/2005 | Grootaert et al. |
| 6,887,927 B2 | 5/2005 | Grootaert et al. |
| 6,890,995 B2 | 5/2005 | Kolb et al. |
| 6,959,085 B1 | 10/2005 | Hoffstein et al. |
| 7,208,553 B2 | 4/2007 | Grootaert et al. |
| 7,214,748 B2 | 5/2007 | Weiss |
| 7,294,677 B2 | 11/2007 | Grootaert et al. |
| 7,402,630 B2 | 7/2008 | Grootaert et al. |
| 7,655,591 B2 * | 2/2010 | Grootaert et al. ............ 502/150 |
| 7,666,949 B2 * | 2/2010 | Grootaert et al. .......... 525/326.3 |
| 7,989,552 B2 * | 8/2011 | Grootaert et al. .......... 525/326.3 |
| 2002/0026014 A1 | 2/2002 | Bish et al. |
| 2002/0061977 A1 | 5/2002 | Grootaert et al. |
| 2002/0145228 A1 * | 10/2002 | Kolb et al. .................... 264/236 |
| 2002/0177666 A1 | 11/2002 | Grootaert et al. |
| 2004/0044139 A1 | 3/2004 | Grootaert et al. |
| 2004/0162395 A1 | 8/2004 | Grootaert et al. |
| 2005/0154145 A1 | 7/2005 | Kolb et al. |
| 2006/0135827 A1 * | 6/2006 | Grootaert et al. ............ 570/123 |
| 2006/0235157 A1 | 10/2006 | Kanega et al. |

FOREIGN PATENT DOCUMENTS

| | | |
|---|---|---|
| EP | 0 584 678 A1 | 3/1994 |
| EP | 0 661 304 A1 | 7/1995 |
| EP | 0 708 084 A1 | 4/1996 |
| EP | 0 727 413 A1 | 8/1996 |
| EP | 0 754 721 A2 | 1/1997 |
| EP | 0 758 668 A2 | 2/1997 |
| EP | 0 769 521 A1 | 4/1997 |
| EP | 0 784 064 A1 | 7/1997 |
| EP | 1 182 230 A1 | 2/2002 |
| JP | 9-183879 | 7/1997 |
| JP | 2004-285264 | 10/2004 |
| WO | WO 90/14368 | 11/1990 |
| WO | WO 98/54253 | 12/1998 |
| WO | WO 99/48939 A1 | 9/1999 |
| WO | WO 00/09569 | 2/2000 |
| WO | WO 00/09603 | 2/2000 |
| WO | WO 01/02448 A1 | 1/2001 |
| WO | WO 01/05710 A1 | 1/2001 |
| WO | WO 01/57100 A1 | 8/2001 |
| WO | WO 01/59005 A2 | 8/2001 |
| WO | WO 02/060969 A1 | 8/2002 |
| WO | WO 2005/000917 A1 | 1/2005 |
| WO | WO 2006/065334 A1 | 6/2006 |
| WO | WO 2007/024869 A2 | 3/2007 |
| WO | WO 2009/111120 A2 | 9/2009 |

OTHER PUBLICATIONS

ASTM: D 1646-04, Standard Test Methods for Rubber-Viscosity, Stress Relaxation, and Pre-Vulcanization Characteristics (Mooney Viscometer), pp. 1-12, published 2005.

Brown et al., "Reactions of Perfluoroalkyl Nitriles. V. Synthesis of Perfluoroacyl Imidates", J. Org. Chem., vol. 30, (1965), pp. 3724-3728.

Farah et al., "Perhalo Ketones. V. The Reaction of Perhaloacetones with Aromatic Hydrocarbons", J. Org. Chem., 1965, vol. 30, pp. 998-1001.

Grinblat et al., "Infrared Investigation of The Vulcanization of Perfluoroalkylenetriazine Polymers", Polymer Science U.S.S.R., vol. 21, 1980, pp. 1434-1441.

Marshall, J.B., "Modern Fluoropolymers—Kalrez—Type Perfluoro-elastomer-Synthesis, Properties and Applications", Wiley Series in Polymer Science, Chapter 19, 1997, pp. 349-359.

Paciorek et al., "Reactions of Perfluoronitriles. I. Interactions with Aniline", Journal of Fluorine Chemistry, 30 (1985), pp. 241-250.

(56) References Cited

OTHER PUBLICATIONS

Yakubovich et al., "Syntheses in the 1,3,5-Triazine Series V. Iminoesters of Perfluorocarboxylic Acids-Synthese, Properties, and Mechanism of Cyclopolymerization to 1,3,5-Triazine Derivatives", pp. 878-885, (translated from Zhurnal Obshchei Khimii, vol. 36, No. 5, pp. 863-871, May 1966).

* cited by examiner

CURING COMPOSITIONS FOR FLUOROPOLYMERS

CROSS REFERENCE TO RELATED APPLICATIONS

This application is a national stage filing under 35 U.S.C. 371 of PCT/US2010/039730, filed Jun. 24, 2010, which claims priority to U.S. Provisional Application No. 61/220,441, filed Jun. 25, 2009, the disclosures of which are incorporated by reference in their entirety herein.

TECHNICAL FIELD

This invention relates to a catalyst composition as well as curable and cured fluoropolymer compositions, methods of making fluoropolymer compositions, and fluoropolymer articles.

BACKGROUND

Fluoroelastomers are cured or crosslinked and generally are tolerant to high temperatures and harsh chemical environments. They are particularly useful as seals, gaskets, and molded parts in systems that are exposed to elevated temperatures and/or corrosive materials. For sealing applications that require resistance to the most extreme conditions, perfluorinated elastomers are used. Such parts are used in applications such as automotive, chemical processing, semiconductor, aerospace, and petroleum industries, among others.

Fluoroelastomers often include a cure-site component to facilitate cure in the presence of a curative or catalyst. One class of useful cure-site components used in perfluoroelastomers includes nitrile group-containing monomers, for which organotin catalysts have been used as curing components. However, such catalysts can leave undesirable extractable metal residues in the cured product and are undesirable for environmental reasons. Ammonia-generating compounds have also been used as a cure system component in fluoroelastomers, but these cure systems lack the desired level of rheology control during processing. Fluoroalkoxy onium containing catalysts were developed to address improved compression set performance. However, these catalysts still lack the desired level of rheology control (i.e. premature curing during processing, often referred to as "scorch") during processing unless additional steps were taken to react these catalysts with additional materials. Surprisingly, it has now been found that the additional steps to reduce scorch in fluoropolymer compounds made using these catalysts are obviated by eliminating the use of hydrocarbon containing alcohol when preparing catalyst compounds or removing the hydrocarbon containing alcohol from the catalyst compounds.

SUMMARY

In one aspect, the invention relates to a catalyst composition comprising a cation and an anion of Formula I:

$$A_n^{q-} Q_p^{m+} \quad (I)$$

wherein m, n, p, and q are positive integers, wherein $m*p = n*q$, wherein $Q^{m+}$ is an organo onium, and $A^{q-}$ is an anion, and provided that at least one $A^{q-}$ is selected from Formula II:

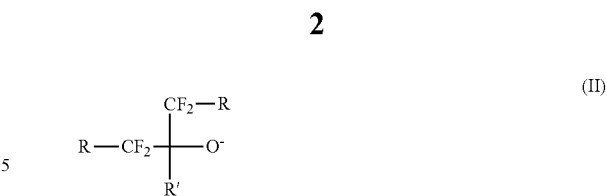

where, in this Formula II, each R independently is H, halo, alkyl, aryl, aralkyl, or cycloalkyl, and which also may be halogenated, fluorinated, or perfluorinated, wherein two or more of R and R' groups may together form a ring, wherein each R group independently may contain one or more heteroatom(s), wherein R' can be the same as R, with the proviso that R' cannot be halo, where the catalyst composition is essentially free of hydrocarbon containing alcohol.

In another aspect, the invention relates to a catalyst composition suitable for fluoroelastomers comprising an anion of Formula III:

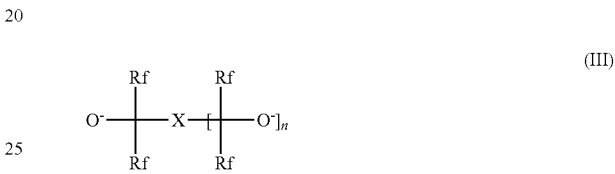

where, in this Formula III, each $R_f$ independently is $R-CF_2$ or a perfluoroalkyl group having from 1 to 8 carbon atoms, wherein R is H, halo, alkyl, aryl, or cycloalkyl, having up to 8 carbon atoms and which also may be halogenated, fluorinated, or perfluorinated, and which may contain a heteroatom, wherein X is a non-fluorinated, partially-fluorinated, or perfluorinated linking group, and wherein n is a positive integer, where the catalyst composition is essentially free of hydrocarbon containing alcohol.

In another aspect, the invention relates to a method of making a catalyst composition such as described above, the method comprising providing a cation and an anion, wherein the anion is prepared by reacting a parent alcohol with a base, such as a tetraalkyl phosphonium hydroxide or tetraalkyl ammonium hydroxide. In another aspect, the anion can be derived by reacting a parent alcohol with a metal hydroxide or alkoxide, such as sodium methoxide, and adding an onium halide, such as an onium chloride, in a solvent, such as a hydrocarbon containing alcohol (i.e. methanol, ethanol, propanol, and the like), and optionally precipitating the resulting halide salt, and removing the solvent.

In another aspect, the invention relates to a fluoroelastomer composition comprising a fluoroelastomer comprising nitrogen-containing cure sites; and a cation and an anion of Formula I:

$$A_n^{q-} Q_p^{m+} \quad (I)$$

wherein m, n, p, and q are positive integers, wherein $m*p = n*q$, wherein $Q^{m+}$ is an organo onium, and $A^{q-}$ is an anion, provided that at least one $A^{q-}$ is selected from Formula II:

where, in Formula II, each R independently is H, halo, alkyl, aryl, aralkyl, or cycloalkyl, and which also may be halogenated, fluorinated, or perfluorinated, wherein two or more of R and R' groups may together form a ring, wherein each R group independently may contain one or more heteroatom(s), wherein R' can be the same as R, with the proviso that R' cannot be halo, where the catalyst composition is essentially free of hydrocarbon containing alcohol.

In another aspect, the invention relates to making a fluoropolymer composition comprising forming a mixture of a catalyst composition as described above, including a fluoroelastomer having interpolymerized units of a nitrogen-containing cure site monomer, and which fluoroelastomer may or may not be perfluorinated. The invention relates to making a fluoropolymer article comprising shaping a mixture of a fluoropolymer composition as described above, curing the shaped mixture to form an article, and optionally post curing the article.

The invention also provides articles containing the curable or cured compositions such as sheets, films, hoses, gaskets, and O-rings. The invention is particularly desirable for articles with good physical properties and low compression set at high temperatures.

The inventive catalyst compositions are, for example, suitable for curing polymers, especially fluoroelastomers. These catalyst compositions typically provide several advantages for curing fluoroelastomers, especially perfluoroelastomers, having nitrogen-containing cure site monomers, such as the high temperature performance properties sought when selecting organotin compounds, ammonia-generating compounds, or even perfluoroadipates as the curative or catalyst system with such fluoroelastomers. In particular, several aspects of the present invention provide or include a class of catalysts that generate triazine crosslinks in perfluoroelastomers more effectively than any known catalyst.

The inventive fluoroelastomer compositions generally maintain the advantages involved with using fluoroelastomers having nitrogen-containing cure site monomers, such as the high temperature performance properties typically achieved when organotin compounds or ammonia-generating compounds are used as the catalyst system with such cure site monomers. Concurrently, the inventive fluoroelastomer compositions may exhibit improved properties, such as better compression set values, compared to materials made using the known organotin compounds, or other known cure catalysts.

The inventive compositions particularly are desirable in applications where high temperature exposure and/or harsh chemical exposure are expected. In some embodiments, the inventive compositions provide a pristine appearance commensurate with their high purity and high quality.

The details of embodiments of the invention are set forth in the description below. Other features, objects, and advantages of the invention will be apparent from the description and from the claims below.

DETAILED DESCRIPTION

The catalyst composition of the present invention involves a cation and an anion. More particularly, the catalyst comprises a composition an anion of Formula I:

$$A_n^{q-} Q^{m+} \quad (I)$$

In this Formula, m, n, p, and q are positive integers, and $m*p=n*q$, such that the charge balances. Additionally, $Q^{m+}$ is an organo onium, and $A^{q-}$ is an anion. At least one $A^{q-}$ is selected from Formula II:

where, in this Formula II, each R independently is H, halo, alkyl, aryl, aralkyl, or cycloalkyl, and which also may be halogenated, fluorinated, or perfluorinated, wherein two or more of R and R' groups may together form a ring, wherein each R group independently may contain one or more heteroatom(s), wherein R' can be the same as R, with the proviso that R' cannot be halo. While not being bound by any particular theory, it is believed that allowing R' to be a halo group would result in it being expelled as a halide anion with subsequent conversion of the parent alkoxide into a carbonyl compound. The presently disclosed catalyst composition is essentially free of hydrocarbon containing alcohol. The term "essentially free" as used herein means less than 5 wt % of hydrocarbon containing alcohol based on the total weight of the catalyst composition, preferably less than 1 wt % of hydrocarbon containing alcohol based on the total weight of the catalyst composition, and more preferably less than 0.1 wt % of hydrocarbon containing alcohol based on the total weight of the catalyst composition. The term "hydrocarbon containing alcohol" as used herein means alcohol that has only hydrogen or carbon substituents on the hydroxyl bearing carbon with the proviso that, in the case where the hydroxyl bearing carbon atom is substituted with another carbon atom, said carbon atom is not also bound to a halogen atom. The hydrocarbon containing alcohol may include halogen atoms as long at these halogen atoms are at least 2 carbon atoms away from the hydroxyl bearing carbon. The presently disclosed hydrocarbon containing alcohol includes, for example, ethanols, methanols, propanols, ethylene glycol, 2-methoxy ethanol, and the like.

For example, each R can be F such that the central carbon of the anion is bonded to two perfluoromethyl groups. In addition, R' can be selected from the group consisting of H, phenyl, methoxyphenyl, toluyl, phenoxy, fluorophenyl, trifluoromethylphenyl, and $CF_3$.

More particularly, the anion can substituted or unsubstituted. Examples include tetra-alkylammonium 2-phenyl-1,1,1,3,3,3 hexafluoroisopropanoate, tetra-alkylammonium 1,1,1,3,3,3 hexafluoroisopropanoate, tetrabutylphosphonium 2-phenyl-1,1,1,3,3,3 hexafluoroisopropanoate, tetrabutylphosphonium 1,1,1,3,3,3 hexafluoroisopropanoate, tetrabutylphosphonium 2-methoxyphenyl-1,1,1,3,3,3 hexafluoroisopropanoate, and tetrabutylphosphonium 2-p-toluyl-1,1,1,3,3,3 hexafluoroisopropanoate.

In another embodiment, the invention provides a catalyst composition suitable for fluoroelastomers comprising an anion of Formula III:

where, in this Formula III, each $R_f$ independently is $R-CF_2$ or a perfluoroalkyl group having from 1 to 8 carbon atoms, wherein R is H, halo, alkyl, aryl, or cycloalkyl, having up to 8 carbon atoms and which also may be halogenated, fluorinated, or perfluorinated, and which may contain a heteroatom, wherein X is a non-fluorinated, partially-fluorinated, or perfluorinated linking group, and wherein n is a positive integer, where the presently disclosed catalyst composition is essentially free of hydrocarbon containing alcohol. The linking group can be aryl, lower alkylene (e.g., C1-C10), and may contain a heteroatom. The linking group may be substituted with halo, lower alkyl (having from 1 to about 10 carbon atoms). With this catalyst, one or more cation(s) can be used to balance the charge. Any suitable cation(s) can be used, as described below.

In another embodiment, the invention provides a catalyst composition suitable for fluoroelastomers comprising a cation and an anion of Formula IV:

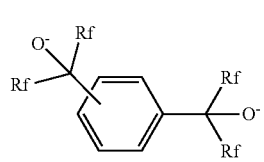

(IV)

where, in this Formula IV, each $R_f$ independently is $R$—$CF_2$ or a perfluoroalkyl group having from 1 to 8 carbon atoms. Also in this Formula, R is H, halo, alkyl, aryl, or cycloalkyl, having up to 8 carbon atoms and which also may be halogenated, fluorinated, or perfluorinated, and which may contain a heteroatom. In addition, the aryl group may be substituted, e.g., with a halo, lower alkyl (e.g., C1-C10), and it may contain a heteroatom.

These inventive catalyst compositions can be used, for example, to cure or crosslink fluoropolymers, such as those described below. Thus, these catalysts can be mixed with fluoroelastomers or perfluoroelastomers.

In another embodiment, the present invention provides a fluoroelastomer composition comprising a fluoroelastomer having interpolymerized units derived from a nitrogen-containing cure site monomer along with a catalyst as will now be described. This catalyst comprises a cation and an anion of Formula I (above) wherein m, n, p, and q are positive integers, wherein m*p=n*q, wherein $Q^{m+}$ is an organo onium, and $A^{q-}$ is an anion, provided that at least one $A^{q-}$ is selected from Formula II (above) wherein each R independently is H, halo, alkyl, aryl, aralkyl, or cycloalkyl, and which also may be halogenated, fluorinated, or perfluorinated, wherein two or more of R and R' groups may together form a ring, wherein each R group independently may contain one or more heteroatom(s), wherein R' can be the same as R, with the proviso that R' cannot be halo, where the catalyst composition is essentially free of hydrocarbon containing alcohol. In one embodiment of the present invention, each $R_f$ is $CF_3$.

Any cation that does not substantially interfere with the desired result can be used. For example, the cation can be organic. As examples, in some embodiments, the cation is an organo onium.

In some embodiments, the fluoropolymer composition may include interpolymerized units derived from tetrafluoroethylene (TFE), chlorotrifluoroethylene (CTFE), and/or one or more ethylenically-unsaturated monomers represented by the formulas $CF_2$=CF—$R_f^1$, $CF_2$=CF—O—$R_f^2$, and $CH_2$=$CR_2$, wherein $R_f^1$ is a perfluoroalkyl; $R_f^2$ is a perfluoroalkyl, or a perfluoroalkoxy; and each R is independently selected from H, F, Br, I, Cl, or a aliphatic group. In some embodiments, the perfluoroalkyl, perfluoroalkoxy, and aliphatic groups may have F, Br, I, or Cl substituents. In some embodiments, the fluoropolymer composition may include interpolymerized units derived from perfluoro alkyl vinyl ether(s), perfluoro alkoxy vinyl ether(s), perfluoro alkene ether(s), and/or perfluoro alkoxy alkene ether(s).

Suitable fluoropolymers include interpolymerized units derived from a nitrogen-containing cure site monomer and, preferably, at least two principal monomers. Examples of suitable candidates for the principal monomer include perfluoroolefins (e.g., tetrafluoroethylene (TFE) and hexafluoropropylene (HFP)), chlorotrifluoroethylene (CTFE), perfluorovinyl ethers (e.g., perfluoroalkyl vinyl ethers and perfluoroalkoxy vinyl ethers), and optionally, hydrogen-containing monomers such as olefins (e.g., ethylene, propylene, and the like), and vinylidene fluoride (VDF). Such fluoropolymers include, for example, fluoroelastomer gums and perfluoroelastomer gums.

When the fluoropolymer is halogenated, preferably perfluorinated, it contains at least 50 mole percent (mol %) of its interpolymerized units derived from TFE and/or CTFE, optionally including HFP. The balance of the interpolymerized units of the fluoropolymer (10 to 50 mol %) is made up of one or more perfluoro vinyl ethers and a nitrogen-containing cure site monomer (e.g., a nitrile-containing vinylether or an imidate containing vinylether). The cure site monomer makes up from about 0.1 to about 5 mol % (more preferably from about 0.3 to about 2 mol %) of the elastomer. The invention is useful particularly in providing perfluoropolymers such as perfluoroelastomers.

When the fluoropolymer is not perfluorinated, it may contain from about 5 to about 90 mol % of its interpolymerized units derived from TFE, CTFE, and/or HFP, from about 5 to about 90 mol % of its interpolymerized units derived from VDF, ethylene, and/or propylene, up to about 40 mol % of its interpolymerized units derived from a vinyl ether, and from about 0.1 to about 5 mol % (more preferably from about 0.3 to about 2 mol %) of a nitrogen-containing cure site monomer.

The fluoroelastomer compositions of the invention are derived from interpolymerized units of fluorinated monomers such as those having the formula $CF_2$=CF—$R_f$, wherein $R_f$ is fluorine or a $C_1$-$C_8$ perfluoroalkyl, along with hydrogen-containing $C_2$-$C_9$ olefins, which have less than half of the hydrogen atoms substituted with fluorine, more preferably less than one-fourth of the hydrogen atoms substituted with fluorine, and which are non-fluorinated in other embodiments. In some embodiments, the non-fluorinated olefin is absent.

Hydrogen-containing olefins useful in the invention include those of the formula $CX_2$=CX—R, wherein each X is, independently, hydrogen or fluorine or chlorine, R is hydrogen, fluorine, or a $C_1$-$C_{12}$, preferably $C_1$-$C_3$, alkyl. Preferred olefins include partially-fluorinated monomers (e.g., vinylidene fluoride) or hydrogen-containing monomers such as olefins including α-olefins (e.g., ethylene, propylene, butene, pentene, hexene, and the like). Combinations of the above-mentioned materials are also useful.

Perfluorinated vinyl ethers also are suitable as comonomers in the present invention. These include, for example, monomers described in U.S. Pat. Nos. 6,255,536 and 6,294,627 (Worm, et al., herein incorporated by reference) which includes perfluorinated vinyl ethers such as $CF_2$=CF$(CF_2)_m$—[$O(CF_2)_p$]$_n$—$OR_f$, including vinyl formals such as $R_f OCF_2 OCF$=$CF_2$, where $R_f$ can contain oxygen, wherein $R_f$ is a linear or branched perfluorinated aliphatic group that may contain oxygen atoms thereby forming additional ether linkages, and wherein m is 0-4, n is 0-6, and p is 1-3, provided that m and n are not both 0.

Such perfluorovinylethers include, for example, $CF_2=CFOCF_3$, $CF_2=CF-O-CF_2-O-CF_3$, $CF_2=CF-O-CF_2-O-CF_2CF_3$, $CF_2=CF-O-CF_2-O-CF_2CF_3$, $CF_2=CFOCF_2CF_2OCF_3$, $CF_2=CFOCF_2CF_2CF_2OCF_3$, $CF_2=CFOCF_2CF_2CF_3$, $CF_2=CF-O-CF_2CF(CF_3)-O-CF_3$, $CF_2=CFOCF_2CF(CF_3)OCF_2CF_2CF_3$, $CF_2=CF-O-CF_2CF_2-O-CF_2-O-CF_2-O-CF_3$, and $CF_2=CFOCF_2CF(CF_3)OCF_2CF(CF_3)OCF_2CF_2CF_3$.

In addition, the fluoropolymers of the invention may include interpolymerized units of fluoro(alkene ether) monomers, including those described in U.S. Pat. No. 5,891,965 (Worm and Guerra) and U.S. Pat. No. 6,255,535 (Schulz, et al.), the disclosures of each of which are herein incorporated by reference. Such monomers include, for example, $CF_2=CF(CF_2)_m-O-R_f$ wherein m is an integer from 1 to 4, and wherein $R_f$ is a linear or branched perfluoroalkylene group that may include oxygen atoms thereby forming additional ether linkages, and wherein $R_f$ contains from 1-20, more preferably from 1 to 10, carbon atoms in the backbone, and wherein $R_f$ also may contain additional terminal unsaturation sites. $R_f$ groups containing such oxygen atoms are referred to as perfluoroalkyleneoxy groups. Useful monomers include the perfluoroallyl ethers represented by the formula: $CF_2=CF-CF_2-O-R_f$, where $R_f$ is defined above in this paragraph. Exemplary perfluoroalkeneether compounds include those selected from the group consisting of $CF_2=CFCF_2-O-CF_3$, $CF_2=CFCF_2-O-CF_2-O-CF_3$, $CF_2=CFCF_2-O-CF_2CF_2-O-CF_3$, $CF_2=CFCF_2-O-CF_2CF_2-O-CF_2-O-CF_2CF_3$, $CF_2=CFCF_2-O-CF_2CF_2-O-CF_2CF_2CF_2-O-CF_3$, $CF_2=CFCF_2-O-CF_2CF_2-O-CF_2CF_2-O-CF_2-O-CF_3$, $CF_2=CFCF_2CF_2-O-CF_2CF_2CF_3$.

One example of a useful fluoropolymer is composed of principal monomer units of tetrafluoroethylene and at least one perfluoroalkyl vinyl ether. In such copolymers, the copolymerized perfluorinated ether units constitute from about 1 to about 60 mol % (more preferably 10 to 40 mol %) of total monomer units present in the polymer.

One or more other fluoropolymers may be incorporated into the fluoropolymer having interpolymerized units derived from a nitrogen-containing cure site monomer. In addition, one or more other fluoropolymers (which may include one or more copolymers) may be blended with the fluoropolymer (which may comprise a copolymer) having interpolymerized units derived from a nitrogen-containing cure site monomer. Such other fluoropolymers useful in a blend and/or copolymer include the entire array described above, and including homopolymers and copolymers comprising the interpolymerized units mentioned above. For example, polytetrafluoroethylene (PTFE) and PFA (tetrafluoroethylene-perfluorovinylether) are useful. The other fluoropolymer(s) may lack interpolymerized units derived from a nitrogen-containing cure site monomer and/or may include reactive sites adapted to a selected curative system. For example, two different fluoropolymers, each having interpolymerized units derived from a nitrogen-containing cure site monomer, such as a monomer comprising a nitrile group, may be blended to provide the fluoropolymer for the present invention.

Another fluoropolymer may be included along with another curative, such as described below, to provide particular properties. For example, a fluoropolymer suitable for peroxide curing and a peroxide curative may be included to improve chemical stability. Such a blend balances the thermal stability and the chemical stability of the resultant blend, and also may provide economic benefits. These other curatives also may be used to cure a blend of fluoropolymers having nitrogen-containing cure site monomers without the need to include a fluoropolymer lacking a nitrogen-containing cure site monomer.

The fluoropolymer(s) having nitrogen-containing cure site monomers preferably make up enough of the total fluoropolymer to provide increased thermal stability over a comparative fluoropolymer that lacks the composition of the present invention. This amount is generally at least 25 weight percent (wt %), more preferably at least 50 wt %, of the total fluoropolymer in the invention. In some embodiments, the fluoropolymer component is comprised entirely of fluoropolymer(s) with nitrogen-containing interpolymerized units.

The useful fluoropolymers may be prepared by known methods. For example, the polymerization process can be carried out by free-radical polymerization of the monomers as an aqueous emulsion polymerization or as a solution polymerization in an organic solvent. When fluoropolymer blends are desired, a preferable route of incorporation is through blending the fluoropolymer latices in the selected ratio, followed by coagulation and drying.

The nature and the amount of end groups in the fluoroelastomers of the invention can vary. For example, the polymer can contain $SO_3^{(-)}$ end groups generated by an APS/sulfite system, or the polymer may contain $COO^{(-)}$ end groups generated by an APS initiator system or the fluoroelastomer can have "neutral", non-ionic end groups, e.g., those generated by the use of fluorosulfinate initiator systems (see U.S. Pat. Nos. 5,378,782 and 5,285,002 which are herein incorporated by reference) or organic peroxides. Chain transfer agents of any kind can significantly reduce the number of ionic or polar end groups. If desired, such as for improved processing, the presence of strong polar end groups such as $SO_3^{(-)}$ can be minimized and in the case of $COO^{(-)}$ or other unstable end groups, the amount can be reduced through known post treatments (e.g., decarboxylation, post-fluorination).

Fluoropolymers of the invention include a cure site component, which enables curing the fluoropolymer. The cure site component can be partially or fully fluorinated. At least one cure site component of at least one fluoropolymer comprises a nitrogen-containing group. Examples of nitrogen-containing groups useful in the cure site monomers of the present invention include nitrile, imidate, amidine, amide, imide, and amine-oxide groups. Useful nitrogen-containing cure site monomers include nitrile-containing fluorinated olefins and nitrile-containing fluorinated vinyl ethers, such as: $CF_2=CFO(CF_2)_LCN$; $CF_2=CFO(CF_2)_uOCF(CF_3)CN$; $CF_2=CF[OCF_2CF(CF_3)]_rO(CF_2)_tCN$; $CF_2=CFO[CF_2CF(CF_3)O]_q(CF_2O)_yCF(CF_3)CN$; and; wherein L=2-12; q=0-4; r=1-2; y=0-6; t=1-4; and u=2-6. Representative examples of such monomers include $CF_2=CFO(CF_2)_3OCF(CF_3)CN$, perfluoro(8-cyano-5-methyl-3,6-dioxa-1-octene), and $CF_2=CFO(CF_2)_5CN$ (MV5CN).

Another suitable cure site component useful in the present invention is a fluoropolymer or fluorinated monomer material containing a halogen that is capable of participation in a peroxide cure reaction. Such a halogen may be present along a fluoropolymer chain and/or in a terminal position. Typically the halogen is bromine or iodine. Copolymerization is preferred to introduce the halogen in a position along a fluoropolymer chain. In this route, a selection of the fluoropolymer components mentioned above are combined with a suitable fluorinated cure site monomer. Examples of the bromo- or iodo-fluoroolefins include: bromodifluoroethylene, bromotrifluoroethylene, iodotrifluoroethylene, 1-bromo-2,2-difluoroethylene, and 4-bromo-3,3,4,4-tetrafluorobutene-1, and the like, and examples of the bromo- or iodo-fluorovinyl ethers include: $BrCF_2OCF=CF_2$, $BrCF_2CF_2OCF=CF_2$, $BrCF_2CF_2CF_2OCF=CF_2$, $CF_3CF(Br)CF_2OCF=CF_2$, and the like. In addition, non-fluorinated bromo- or iodo-olefins, e.g., vinyl bromide and 4-bromo-1-butene, can be used.

The amount of cure site component in a side chain position of the fluoropolymer generally is from about 0.05 to about 5 mol % (more preferably from 0.1 to 2 mol %).

The cure site component may also occur in the terminal position of a fluoropolymer chain. Chain transfer agents or initiators are used to introduce the halogen in a terminal position. Generally, a suitable chain transfer agent is introduced in the reaction medium during polymer preparation, or derived from a suitable initiator.

Examples of useful chain transfer agents include those having the formula $R_fZ_x$ wherein $R_f$ is a substituted or unsubstituted $C_1$-$C_{12}$ fluoroalkyl radical, which may be perfluorinated, Z is Br or I, and x is 1 or 2. Specific examples involving bromide include: $CF_2Br_2$, $Br(CF_2)_2Br$, $Br(CF_2)_4Br$, $CF_2(Cl)Br$, $CF_3CF(Br)CF_2Br$, and the like.

Useful initiators include, e.g., $NaO_2S(CF_2)_nX$, wherein X is Br or I, and n is 1-10.

The amount of cure site component in a terminal position in the fluoropolymer is generally from about 0.05 to about 5 mol % (more preferably from 0.1 to 2 mol %).

Combinations of cure site components also are useful in the present invention. For example, a fluoropolymer containing a halogen that is capable of participation in a peroxide cure reaction may also contain a nitrogen-containing cure site component such as a nitrile group-containing cure site component. Generally, from about 0.1 to about 5 mol % (more preferably from about 0.3 to about 2 mol %) of the total cure site component is incorporated into the fluoropolymer.

An effective amount of the catalyst is used to crosslink the fluoropolymer. When the amount of catalyst is too low, the fluoropolymer may not crosslink sufficiently to develop the desired physical properties and/or may crosslink more slowly than desired. When the amount of catalyst is too high, the fluoropolymer may crosslink into a material that is less compliant than desired and/or may crosslink too rapidly for the desired process conditions. The selection of the particular parts of a composition can affect the amount of catalyst desired. For example, the type and/or amount of filler selected may retard or accelerate curing relative to a similar, but unfilled, composition, requiring an appropriate adjustment in the amount of curative that is known to those skilled in the field. In another example, when the catalyst is hygroscopic, the type and/or amount of filler in the catalyst composition may alter the hygroscopicity of the catalyst composition.

The composition of the fluoropolymer also affects the desired amount of one or more catalysts. For example, when a blend of a fluoropolymer with interpolymerized units of a nitrogen-containing cure site monomer and another fluoropolymer lacking nitrogen-containing cure sites is used, an effective amount of a first selected catalyst compound can be used to crosslink the fluoropolymer having interpolymerized units derived from a nitrogen-containing cure site monomer together with an effective amount of a second selected catalyst compound used to crosslink the other fluoropolymer. The first and second selected catalysts may have the same or different composition. That is, either one or both selected catalysts may function to crosslink either one or both fluoropolymers.

Generally, the effective amount of catalysts, which may include more than one composition, is at least about 0.1 parts curative per hundred parts of gum on a weight basis (phr), preferably at least about 0.5 phr. The effective amount of curative generally is below about 10 phr, preferably below about 5 phr.

The fluoropolymer composition curing can also be modified by using other types of curatives along with the catalyst of the present invention. Examples of such curatives are known and include bis-aminophenols (e.g., U.S. Pat. Nos. 5,767,204 and 5,700,879), bis-amidooximes (e.g., U.S. Pat. No. 5,621,145), and ammonium salts (e.g., U.S. Pat. No. 5,565,512). In addition, organometallic compounds of arsenic, antimony, and tin can be used (e.g., U.S. Pat. Nos. 4,281,092, and 5,554,680). Particular examples include allyl-, propargyl-, triphenyl-allenyl-, and tetraphenyltin and triphenyltin hydroxide. The disclosures of each of these documents is herein incorporated by reference.

The fluoroelastomer compositions of the invention can be cured using one or more ammonia-generating compounds along with the curatives described above. "Ammonia-generating compounds" include compounds that are solid or liquid at ambient conditions but that generate ammonia under conditions of cure. Such compounds include, for example, hexamethylenetetramine(urotropin), dicyandiamide, and metal-containing compounds of the formula $A^{w+}(NH_3)_xY^{w-}$, wherein $A^{w+}$ is a metal cation such as $Cu^{2+}$, $Co^{2+}$, $Co^{3+}$, $Cu^+$, and $Ni^{2+}$; w is equal to the valance of the metal cation; $Y^{w-}$ is a counterion, typically a halide, sulfate, nitrate, acetate or the like; and x is an integer from 1 to about 7.

Also useful as ammonia-generating compounds are substituted and unsubstituted triazine derivatives such as those of the formula:

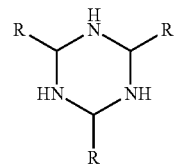

wherein R is a hydrogen atom or a substituted or unsubstituted alkyl, aryl, or aralkyl group having from 1 to about 20 carbon atoms. Specific useful triazine derivatives include hexahydro-1,3,5-s-triazine and acetaldehyde ammonia trimer.

The fluoroelastomer compositions of the invention, including the nitrogen-containing cure site monomer-containing fluoropolymer alone, can be cured using one or more peroxide curatives along with a curative as described above. Suitable peroxide curatives generally are those which generate free radicals at curing temperatures, such as those described in WO 99/48939, the disclosure of which is herein incorporated by reference. Dialkyl peroxide and bis(dialkyl peroxide), each of which decomposes at a temperature above 50° C., are especially preferred. In many cases it is preferred to use a di-tertiarybutyl peroxide having a tertiary carbon atom attached to peroxy oxygen atom. Among the most useful peroxides of this type are 2,5-dimethyl-2,5-di(tertiarybutylperoxy)hexyne-3 and 2,5-dimethyl-2,5-di(tertiarybutylperoxy)hexane. Other peroxides can be selected from such compounds as dicumyl peroxide, dibenzoyl peroxide, tertiarybutyl perbenzoate, a,a'-bis(t-butylperoxy-diisopropylbenzene), and di[1,3-dimethyl-3-(t-butylperoxy)-butyl]carbonate. Generally, about 1 to 3 parts of peroxide per 100 parts of perfluoroelastomer is used.

Another combination curative useful in the present invention has the general formula $CH_2=CHR_fCH=CH_2$, wherein one or more H atoms may be replaced with halogen atoms, such as F, and $R_f$ is a $C_1$-$C_8$ linear or branched and at least partially fluorinated alkylene, cycloalkylene, or oxyalkylene. Similarly, polymers containing pendant groups of $CH_2=CHR_f$— are also useful as curatives in the present invention. Such curatives are described, for example, in U.S. Pat. No. 5,585,449.

The combination of curative(s) is generally from about 0.01 to about 10 mol % (more preferably from about 0.1 to about 5 mol %) of the total fluoropolymer amount.

The fluoropolymer compositions can include any of the adjuvants commonly employed in curable fluoropolymer formulations. For example, one material often blended with a fluoropolymer composition as a part of a curative system is a coagent (sometimes also referred to as a co-curative) composed of a polyunsaturated compound that is capable of cooperating with the peroxide curative to provide a useful cure. These coagents are particularly useful in combination with a peroxide curative. The coagent(s) can generally be added in an amount equal to between 0.1 and 10 parts coagent per hundred parts fluoropolymer (phr), preferably between 1 and 5 phr. Examples of coagents useful with the present invention include triallyl cyanurate; triallyl isocyanurate; tri(methylallyl)isocyanurate; tris(diallylamine)-s-triazine; triallyl phosphite; N,N-diallyl acrylamide; hexaallyl phosphoramide; N,N,N',N'-tetraalkyl tetraphthalamide; N,N,N',N'-tetraallyl malonamide; trivinyl isocyanurate; 2,4,6-trivinyl methyltrisiloxane; and tri(5-norbornene-2-methylene)cyanurate. Particularly useful is triallyl isocyanurate. Other useful coagents include the bis-olefins disclosed in EP0661304A1, EP0784064A1, EP0769521A1, and U.S. Pat. No. 5,585,449, which are herein incorporated by reference.

Thus, a particular composition of the present invention may include two or more fluoropolymer(s) (provided that at least one fluoropolymer includes interpolymerized units derived from a nitrogen-containing cure site monomer), an amidine curative, a peroxide curative selected to crosslink one or more than one of the fluoropolymer(s), and optionally a coagent such as triallyl isocyanurate.

Additives such as carbon black, stabilizers, plasticizers, lubricants, fillers including silica and fluoropolymer fillers (e.g., PTFE and/or PFA (perfluoroalkoxy) fillers), and processing aids typically utilized in fluoropolymer compounding can be incorporated into the compositions, provided that they have adequate stability for the intended service conditions. In some embodiments, additives that detrimentally affect the clarity of the composition are avoided. In particular, low temperature performance can be enhanced by incorporation of perfluoropolyethers, as described above.

Fillers such as silica and/or carbon black fillers can be used to balance properties such as modulus, tensile strength, elongation, hardness, abrasion resistance, conductivity, and processability of the compositions. Suitable examples include fumed silica, such as, for example fumed silica commercially available under the trade designation "Aerosil" from Degussa AG, and carbon blacks such as MT blacks (medium thermal black) designated N-991, N-990, N-908, and N-907; FEF N-550; and large particle size furnace blacks. When carbon black is used, 1 to 70 parts filler per hundred parts fluoropolymer (phr) generally is sufficient.

One of the advantages of selected embodiments of the present invention is a fluoropolymer, such as a fluoroelastomer or a perfluoroelastomer, that provides a desired level of rheology control in that it is not scorchy, or does not prematurely cure, during processing, without additional processing steps to react the catalyst compound with other materials.

One or more acid acceptors can also be added to the formulations. However, where the presence of extractable metallic compounds is undesirable (such as for semiconductor applications) the use of inorganic acid acceptors can be minimized, and or avoided altogether. Commonly used acid acceptors include, for example, zinc oxide, calcium hydroxide, calcium carbonate, magnesium oxide, silicon dioxide (silica), etc. These compounds generally are used in the fluoropolymer formulation to bind any HF or other acids that might be generated at the high temperatures such as may be encountered during curing steps or at the temperatures of fluoropolymer end use.

The curable fluoropolymer compositions of the invention may also be combined with other curable fluoropolymer compositions such as peroxide-curable fluoropolymer compositions. These additional curable fluoropolymer compositions may also employ small amounts of cure site monomers as a comonomer. Suitable cure site monomers are those which, when combined with a curative (e.g., a peroxide) and, preferably a coagent, will provide a cured composition. Preferably these cure site monomers include at least one halo group (e.g., a bromo or an iodo group).

The curable fluoropolymer compositions can be prepared by mixing one or more fluoropolymer(s), the catalyst, any selected additive or additives, any additional curatives (if desired), and any other adjuvants (if desired) in conventional rubber processing equipment. The desired amounts of compounding ingredients and other conventional adjuvants or ingredients can be added to the unvulcanized fluorocarbon gum stock and intimately admixed or compounded therewith by employing any of the usual rubber mixing devices such as internal mixers, (e.g., Banbury mixers), roll mills, or any other convenient mixing device. The temperature of the mixture during the mixing process typically is kept safely below the curing temperature of the composition. Thus, the temperature typically should not rise above about 120° C. During mixing, it generally is preferable to distribute the components and adjuvants uniformly throughout the gum.

The mixture is then processed and shaped, such as by extrusion (e.g., into the shape of a film, tube, or hose) or by molding (e.g., in the form of sheet or an O-ring). The shaped article can then be heated to cure the fluoropolymer composition and form a cured article.

Molding or press curing of the compounded mixture usually is conducted at a temperature sufficient to cure the mixture in a desired time duration under a suitable pressure. Generally, this is between about 95° C. and about 230° C., preferably between about 150° C. and about 205° C., for a period of from about 1 minute to 15 hours, typically from 5 minutes to 30 minutes. A pressure of between about 700 kPa and about 21,000 kPa is usually imposed on the compounded mixture in a mold. The molds may be first coated with a release agent and baked.

The molded mixture or press-cured article is then usually post-cured (e.g., in an oven) at a temperature and for a time sufficient to complete the curing, usually between about 150° C. and about 300° C., typically at about 230° C., for a period of from about 2 hours to 50 hours or more, generally increasing with the cross-sectional thickness of the article. For thick sections, the temperature during the post cure is usually raised gradually from the lower limit of the range to the desired maximum temperature. The maximum temperature used is preferably about 300° C., and this value is held for about 4 hours or more. This post-cure step generally completes the cross-linking and may also release residual volatiles from the cured compositions. One example of a suitable post-cure cycle involves exposing molded parts to heat under nitrogen using six stages of conditions. First, the temperature is increased from 25° C. to 200° C. over 6 hours, then the parts are held at 200° C. for 16 hours, after which the temperature is increased from 200° C. to 250° C. over 2 hours. Then the parts are held at 250° C. for 8 hours, after which the temperature is increased from 250° C. to 300° C. over 2 hours. Then the parts are held at 300° C. for 16 hours. Finally, the parts are returned to ambient temperature such as by shutting off the oven heat.

In the various aspects of the invention, the catalyst composition and/or components thereof, such as the cations, are selected to reduce or eliminate detrimental effects in the desired articles and uses. Surprisingly, it is discovered that curable compositions according to the present invention typically have an enhanced processing window as compared to corresponding compositions where the catalyst compound includes at least one hydrocarbon containing alcohol. This is observed, for example in Mooney scorch times as determined by ASTM D 1646-04 "Standard Test Methods for Rubber—Viscosity, Stress Relaxation, and Pre-Vulcanization Characteristics (Mooney Viscometer)", the disclosure of which is incorporated herein by reference. For example, the presently disclosed fluoroelastomer compositions may have a Mooney Scorch Time ($t_{18}$) of at least 15 minutes according to ASTM D1646-96.

The fluoropolymer compositions are useful in production of articles such as O-rings, gaskets, tubing, and seals, especially when a clear perfluoroelastomer article is desired. Such articles are produced by molding a compounded formulation of the fluoropolymer composition with various additives under pressure, curing the article, and then subjecting it to a post-cure cycle. The curable compositions formulated without inorganic acid acceptors are particularly well suited for applications such as seals and gaskets for manufacturing semiconductor devices, and in seals for high temperature automotive uses.

The invention will now be described further by way of the following examples.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used in the following examples: g=grams, min=minutes, mol=mole; mmol=millimole, phr=parts per hundred parts of rubber, hr=hour, ° C.=degrees Celsius, mL=milliliter, L=liter, psi=pounds per square inch, MPa=megapascals, FTNMR=Fourier transform nuclear magnetic resonance, and N-m=Newton-meter.

The following abbreviations are used throughout the Examples:

| ABBREVIATION | DESCRIPTION |
|---|---|
| TFE | Tetrafluoroethylene |
| PMVE | Perfluoro(methyl vinyl ether) |
| MV5CN | $CF_2=CFO(CF_2)_5CN$ |
| TBPTHI1 | tetrabutylphosphonium 2-(p-toluyl)-1,1,1,3,3,3-hexafluoroisopropoxide made with methanol |
| TBPTHI2 | tetrabutylphosphonium 2-(p-toluyl)-1,1,1,3,3,3-hexafluoroisopropoxide made without methanol |
| Fluoropolymer A | copolymer of 65.7 mole percent TFE, 33.0 mole percent PMVE and 1.3 mole percent MV5CN made via aqueous emulsion polymerization. |

Preparation of 2-(p-toluyl)-1,1,1,3,3,3-hexafluoroisopropanol, $CH_3C_6H_4C(CF_3)_2OH$ A 600-mL Parr reactor was loaded with 12 g of $AlCl_3$ (0.09 mol, obtained from Fluka Chemika) and 326 g of toluene (3.5 mol). The reactor was evacuated and 203 g of hexafluoroacetone (1.22 mol, obtained from SynQuest Laboratories, Inc.) was added over 1.5 hr with stirring at room temperature. The reaction exothermed to 45° C. with a pressure rise up to 49 psi (340 kPa). The reaction was completed after one hour, accompanied by a drop in temperature and pressure. The product mixture was washed twice with 600 ml of water. The organic phase was dried with anhydrous $MgSO_4$, filtered and distilled at 174-176° C. to give 228 g of 2-(p-toluyl)-1,1,1,3,3,3-hexafluoroisopropanol.

Catalyst Preparation

Comparative Preparation of Tetrabutylphosphonium 2-(p-toluyl)-1,1,1,3,3,3-hexafluoroisopropoxide (TBPTHI1), $CH_3C_6H_4C(CF_3)_2O^{-+}P(C_4H_2)_4$ with Methanol A 500-mL round bottom flask equipped with a stir bar was charged with 51 g of 2-(p-toluyl)-1,1,1,3,3,3-hexafluoroisopropanol (0.2 mol, made as described under "Preparation of 2-(p-toluyl)-1,1,1,3,3,3-hexafluoroisopropanol, $CH_3C_6H_4C(CF_3)_2OH$") and 42 g of 25 weight percent sodium methoxide in methanol (0.2 mol) was added and heated to a slight methanol reflux. The flask was cooled to room temperature, and a solution of 66 g of tetrabutylphosphonium bromide (0.2 mol) in 66 g of methanol was added. The mixture was heated slightly and stirred for 0.5 hours. The solvent was vacuum stripped and the viscous oil was extracted with diethyl ether and the sodium bromide was filtered out. TBPTHI1 (101 g) was obtained after vacuum stripping the solvent. The presence of residual methanol in the TBPTHI1 was confirmed by FT-NMR spectroscopy.

Example Preparation of Tetrabutylphosphonium 2-(p-toluyl)-1,1,1,3,3,3-hexafluoroisopropoxide (TBPTHI2), $CH_3C_6H_4C(CF_3)_2O^{-+}P(C_4H_2)_4$ without Methanol To a 65.37 gram sample of 2-(p-toluyl)-1,1,1,3,3,3-hexafluoroisopropanol (available from Oakwood Research Chemicals, West Columbia, S.C.) and 200 mL of toluene was added 175 grams of tetrabutylphosphonium hydroxide (40% solution in water). The mixture exothermed from 21° C. to 29° C. during the approximately one minute addition. The mixture was stirred at room temperature for one hour and then stripped on a rotary evaporator with a 40° C. water bath and an aspirator vacuum for 30 minutes. 200 mL toluene was then added to resulting solid to azeotrope the residual water at 40° C. for 30 minutes under water aspirator vacuum. This was repeated several times to obtain an off white solid of TBPTHI2 (122.53 grams; 93.67% yield; m.p. 88° C.; 0.09% residual water by Karl-Fisher titration). The structure was confirmed by FT-NMR spectroscopy.

Example 1

Fluoropolymer A (100 phr) was compounded on a two roll mill with the addition of 0.75 phr of TBPTHI2, 1.5 phr silica available under the trade designation "AEROSIL R972" from Degussa AG, Düsseldorf, Germany, and 30 phr carbon black available under the trade designation "N-990" from Cabot, Boston, Mass. as indicated in Table 1. The compounded mixture was press-cured at 177° C. for 15 minutes. Subsequently the molded test sheets and O-rings were post-cured in air via a step-post-cure (room temperature to 200° C. over 45 min, hold at 200° C. for 2 hr, ramp to 250° C. over 30 min, hold at 250° C. for 2 hr, ramp to 300° C. over 30 min and hold at 300° C. for 4 hr).

After press-cure and post-cure, physical properties were measured with dumbbells cut from a post-cured test slab.

Comparative Example A

Comparative Example A was compounded, molded, press and post cured as in Example 1 but using TBPTHI1 and amounts of components as indicated in Table 1.

After press-cure and post-cure, physical properties were measured with dumbbells cut from a post-cured test slab.

TABLE 1

| COMPONENT | EX. 1 | COMP. EX. A |
|---|---|---|
| Fluoropolymer A, phr | 100 | 100 |
| TBPTHI1, phr | 0.75 | 0 |
| TBPTHI2, phr | 0 | 1.3 |
| N-990, phr | 30 | 30 |
| AEROSIL R972, phr | 1.5 | 1.5 |

Results

Rheology, physical properties, compression set and scorch are shown in Tables 2-5. Cure rheology tests were carried out using uncured, compounded samples using a rheometer marketed under the trade designation Monsanto Moving Die Rheometer (MDR) Model 2000 by Monsanto Company, Saint Louis, Mo., in accordance with ASTM D 5289-93a at 177° C., no pre-heat, 30 minute elapsed time, and a 0.5 degree arc. Both the minimum torque ($M_L$) and highest torque attained during a specified period of time when no plateau or maximum torque was obtained ($M_H$) were measured. Also measured were the time for the torque to increase 2 units above $M_L$ ($t_S2$), the time for the torque to reach a value equal to $M_L+0.5(M_H-M_L)$, (t'50), and the time for the torque to reach $M_L+0.9(M_H-M_L)$, (t'90). Results are reported in Table 2 (below).

TABLE 2

| | EX. 1 | COMP. EX. A |
|---|---|---|
| $M_L$, in-lb (N-m) | 2.70 (1.185) | 2.08 (0.235) |
| $M_H$, in-lb (N-m) | 11.63 (1.315) | 6.36 (0.719) |
| $t_S2$, min | 2.96 | 4.10 |
| t'50, min | 5.05 | 4.35 |
| t'90, min | 11.14 | 9.35 |

Press-cured sheets (150 mm×150 mm×2.0 mm) of the curable compositions prepared in Example 1 and Comparative Example A, except where indicated in Tables 3 and 4, were prepared for physical property determination by pressing at a pressure of about 6.9 MPa and a temperature of 177° C. for 15 min. Press-cured sheets were post-cured by exposure to heat under air using the program detailed in the examples. All specimens were returned to ambient temperature before testing.

Physical Properties

Tensile strength at break, elongation at break, and modulus at 100% elongation were determined according to ASTM D 412-92 using samples cut from the corresponding specimen using ASTM Die D.

Table 3 (below) reports physical properties of the press-cured and post-cured sheets of the curable compositions of Example 1 and Comparative Example A.

TABLE 3

| | EX. 1 | COMP. EX. A |
|---|---|---|
| Tensile Strength at Break, MPa (psi) | 13.6 (1977) | 12.2 (1770) |
| Elongation at Break, % | 218 | 199 |
| 100% Modulus, MPa (psi) | 7.9 (1156) | 8.9 (1300) |

Specimens of the curable compositions of Examples 1 and Comparative Example A, except where indicated in Table 4, were press-cured and post-cured to form O-rings having a cross-section thickness of 0.139 inch (3.5 mm). Compression set of O-ring specimens was measured using ASTM 395-89 Method B. Results are reported in Table 4 (below) as a percentage of permanent set, and were measured at 25% deflection.

TABLE 4

| | EX. 1 | COMP. EX. A |
|---|---|---|
| Compression set after 72 hr at 316° C., % | 34 | 40 |

Mooney Scorch measurements were made at 121° C., following the procedure described in ASTM D 1646-96. The procedure used employed a one minute preheat, the small rotor size and additionally measured the $t_{10}$ and $t_{18}$ value.

Table 5 (below) reports Mooney scorch test results for curable compositions of Example 1 and Comparative Example A.

TABLE 5

| | EX. 1 | COMP. EX. A |
|---|---|---|
| Minimum viscosity units | 95.2 | 94.1 |
| t-3 (min) | 2.28 | 4.31 |
| t-10 (min) | >60 | 8.99 |
| t-18 (min) | >60 | 12.1 |

Various modifications and alterations of this invention may be made by those skilled in the art without departing from the scope and spirit of this invention, and it should be understood that this invention is not to be unduly limited to the illustrative embodiments set forth herein.

We claim:
1. A catalyst composition comprising
a catalyst selected from tetra-alkylammonium 2-phenyl-1,1,1,3,3,3 hexafluoroisopropanoate, tetra-alkylammonium 1,1,1,3,3,3 hexafluoroisopropanoate, tetrabutylphosphonium 2-phenyl-1,1,1,3,3,3 hexafluoroisopropanoate, tetrabutylphosphonium 1,1,1,3,3,3 hexafluoroisopropanoate, tetrabutylphosphonium 2-methoxyphenyl-1,1,1,3,3,3 hexafluoroisopropanoate, and tetrabutylphosphonium 2-p-toluyl-1,1,1,3,3,3 hexafluoroisopropanoate, and wherein the catalyst composition is free of hydrocarbon containing alcohol.

2. The composition of claim 1 further comprising an organic or inorganic filler.

3. A fluoropolymer composition comprising a fluoropolymer and the catalyst composition of claim 1 wherein the fluoropolymer composition is free of hydrocarbon containing alcohol.

4. A fluoroelastomer composition comprising:
a fluoroelastomer comprising nitrogen-containing cure sites; and
the catalyst composition of claim 1 wherein the fluoroelastomer composition is free of hydrocarbon containing alcohol.

5. The fluoroelastomer composition of claim 4 wherein the fluoroelastomer composition has a Mooney scorch time ($t_{18}$) of at least 15 minutes according to ASTM D1646-96.

6. A fluoroelastomer composition comprising the catalyst composition of claim 1 and a fluoroelastomer, which may be perfluorinated, having interpolymerized units of a nitrogen-containing cure site monomer, which may be a nitrile-containing cure site monomer wherein the fluoroelastomer composition is free of hydrocarbon containing alcohol.

7. The fluoroelastomer composition of claim 4 further comprising a filler, optionally wherein the filler is selected from PTFE and/or perfluoroalkoxy/TFE copolymer (PFA).

8. The fluoroelastomer composition of claim 4 wherein the fluoroelastomer comprises interpolymerized units of tetrafluoroethylene and a perfluoroalkylvinylether, perfluoroalkoxyvinylether, perfluoroalkeneether, and/or perfluoroalkoxyalkeneether.

9. The fluoroelastomer composition according to claim 4 wherein the fluoroelastomer comprises interpolymerized units derived from tetrafluoroethylene, a fluorinated comonomer, and optionally one or more perfluorovinyl ethers.

10. A fluoroelastomer composition according to claim 9 wherein the fluorinated comonomer is selected from perfluoroolefins, partially-fluorinated olefins, non-fluorinated olefins, vinylidene fluoride, and combinations thereof.

11. A fluoroelastomer composition according to claim 4 wherein said cure site monomer is selected from a compound of the formula $CF_2=CFO(CF_2)_LCN$; $CF_2=CFO(CF_2)_uOCF(CF_3)CN$; $CF_2=CFO[CF_2CF(CF_3)O]_q(CF_2O)_yCF(CF_3)CN$; or $CF_2=CF[OCF_2CF(CF_3)]_rO(CF_2)_tCN$; wherein L=2-12; q=0-4; r=1-2; y=0-6; t=1-4, and u=2-6; perfluoro(8-cyano-5-methyl-3,6-dioxa-1-octene), and $CF_2=CFO(CF_2)_5CN$.

12. A fluoroelastomer composition according to claim 4 further comprising a filler, optionally selected from fluoropolymer filler, silica, carbon black, and combinations thereof.

13. The fluoroelastomer composition of claim 4 further comprising an additional curative, optionally wherein the additional curative is selected from ammonia-generating compounds, substituted triazine derivatives, unsubstituted triazine derivatives, peroxides, bis-aminophenols, bis-amidooximes, an organotin compound, or an amidine, bis-amidine, tris-amidine, or tetra-amidine, or a salt thereof.

14. A shaped article comprising the fluoroelastomer composition of claim 4.

15. A shaped article comprising the fluoroelastomer composition of claim 4.

16. The composition of claim 5 further comprising a fluoropolymer having interpolymerized units derived from monomers selected from the group consisting of perfluoroolefins, partially-fluorinated olefins, non-fluorinated olefins, vinylidene fluoride, perfluoroalkeneethers, and combinations thereof.

17. The composition of claim 16 further comprising a material selected from ammonium salts, ammonia-generating compounds, substituted triazine derivatives, unsubstituted triazine derivatives, peroxides optionally with a coagent, bis-aminophenols, bis-amidooximes, an organotin compound, or an amidine, bis-amidine, tris-amidine, or tetra-amidine, or a salt thereof; and wherein the coagent optionally is selected from triallyl cyanurate; triallyl isocyanurate; tri (methylallyl) isocyanurate; tris(diallylamine)-s-triazine;
triallyl phosphite; N,N-diallyl acrylamide; hexaallyl phosphoramide; N,N,N',N'-tetraalkyl tetraphthalamide; N,N,N',N'- tetraallyl malonamide; trivinyl isocyanurate; 2,4,6-trivinyl methyltrisiloxane; and tri(5-norbornene-2-methylene)cyanurate.

18. A method of making a fluoropolymer composition comprising: forming a mixture comprising a catalyst composition according to claim 1 and a fluoroelastomer having interpolymerized units of a nitrogen-containing cure site monomer, which may be perfluorinated wherein the fluoroelastomer composition is free of hydrocarbon containing alcohol.

19. A method of making a fluoropolymer article comprising:
(a) providing the mixture of claim 18,
(b) shaping the mixture;
(c) curing the shaped mixture to form an article; and optionally post-curing the article.

20. A method of making a fluoropolymer composition comprising: forming a mixture comprising a composition according to claim 4.

21. A method of making a fluoropolymer article comprising:
(a) forming a mixture comprising a composition according to claim 20;
(b) shaping the mixture;
(c) curing the shaped mixture to form an article; and optionally post-curing the article.

22. A method of making the catalyst of claim 1, comprising providing a cation and an anion, wherein the anion is prepared by:
(i) reacting a parent alcohol with a base, the base optionally being selected from a tetraalkyl phosphonium hydroxide or tetraalkyl ammonium hydroxide; or
(ii) reacting a parent alcohol with a metal hydroxide or alkoxide, optionally selected from sodium methoxide, and in a solvent, adding an onium halide, optionally selected from an onium chloride, and removing the solvent, and optionally precipitating a salt.

23. A method of making the catalyst of claim 1, comprising providing a cation and an anion, wherein the anion is prepared by:
(i) reacting a parent alcohol with a base, the base optionally being selected from a tetraalkyl phosphonium hydroxide or tetraalkyl ammonium hydroxide; or
(ii) reacting a parent alcohol with a metal hydroxide or alkoxide, optionally selected from sodium methoxide, and in a solvent, adding an onium halide, optionally selected from an onium chloride, and removing the solvent, and optionally precipitating a salt.

* * * * *